United States Patent
Liu et al.

(10) Patent No.: US 10,246,514 B2
(45) Date of Patent: Apr. 2, 2019

(54) SINGLE DOMAIN ANTIBODIES THAT BIND TO HUMAN CD20

(71) Applicant: The United States of America, as represented by the Secretary of the Navy, Washington, DC (US)

(72) Inventors: Jinny Lin Liu, Ellicott City, MD (US); Daniel Zabetakis, Brandywine, MD (US); Ellen R. Goldman, Germantown, MD (US); George P. Anderson, Bowie, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/701,530

(22) Filed: Sep. 12, 2017

(65) Prior Publication Data

US 2018/0079822 A1 Mar. 22, 2018

Related U.S. Application Data

(60) Provisional application No. 62/393,412, filed on Sep. 12, 2016.

(51) Int. Cl.
| | |
|---|---|
| *C12P 21/08* | (2006.01) |
| *C07K 16/00* | (2006.01) |
| *C07K 16/28* | (2006.01) |
| *A61K 38/17* | (2006.01) |
| *A61K 39/395* | (2006.01) |
| *A61K 39/00* | (2006.01) |

(52) U.S. Cl.
CPC ........ *C07K 16/2887* (2013.01); *A61K 38/177* (2013.01); *A61K 39/39533* (2013.01); *A61K 2039/505* (2013.01); *C07K 2317/565* (2013.01); *C07K 2317/569* (2013.01); *C07K 2317/92* (2013.01); *C07K 2317/94* (2013.01)

(58) Field of Classification Search
CPC .............. A61K 2039/505; A61K 38/00; C07K 2319/00
See application file for complete search history.

(56) References Cited

PUBLICATIONS (Paul, William E., Fundamental Immunology, 3rd Edition, Raven Press, New York, Chap. 8, pp. 292-295 (1993).*
Rudikoff et al. (Proc. Natl. Acad. Sci. USA, 79(6):1979-1983, Mar. 1982).*
Colman P. M. (Research in Immunology, 145:33-36, 1994).*
Bendig M. M. (Methods: A Companion to Methods in Enzymology, 1995; 8:83-93).*
MacCallum et al. (J. Mol. Biol., 262, 732-745, 1996).*
Casset et al. (Biochemical and Biophysical Research Communications, 307:198-205, 2003).*

* cited by examiner

*Primary Examiner* — Gary B Nickol
*Assistant Examiner* — Lakia J Jackson-Tongue
(74) *Attorney, Agent, or Firm* — US Naval Research Laboratory; Roy Roberts (57) ABSTRACT

Described herein is the development of recombinant single domain antibodies, also known as nanobodies, that may provide better therapeutic results or be useful for diagnostic applications of B-cell lymphomas, or in other applications where an antibody to CD20 may be useful.

6 Claims, 3 Drawing Sheets

Specification includes a Sequence Listing.

SINGLE DOMAIN ANTIBODIES THAT BIND TO HUMAN CD20

CROSS-REFERENCE TO RELATED APPLICATIONS

This Application claims the benefit of U.S. Provisional Application 62/393,412 filed on Sep. 12, 2016, the entirety of which is incorporated herein by reference.

BACKGROUND

Human CD20 is highly expressed in B-lymphoma cells and B-lymphocytes. Once expressed, CD20 remains on cell surface without being internalized or secreted. Moreover, antibody (Abs) binding to CD20 trigger apoptotic cell signaling resulting in the cell death. These attributes make CD20 an ideal therapeutic target for B-lymphomas. Many monoclonal antibodies specifically binding to extracellular large loop formed by residues 142-187 of human CD20 are developed and commonly used for treating non-Hodgkin's lymphoma. The US Food and Drug Administration approved a monoclonal antibody, Rituximab (RTX), a human/mouse chimeric anti-CD20 antibody, for the treatment of B-cell Non-Hodgkin lymphomas (NHLs) in 1997. RTX has been widely used in treating patients with B-cell lymphomas, but only 10% of the treated patients have complete responses. RTX has also for the treatment of auto-immune diseases, such as rheumatoid arthritis. Thus, there is still a need to develop alternative CD20 specific Ab that may provide better therapeutic results or be useful for diagnostic applications.

Single domain antibodies (sdAb, also called nanobodies) are small antigen binding domains (~15 kD) with better penetration in tissues than intact conventional antibodies. Nanobodies are encoded by variable regions of heavy chain variable region (VHH) DNA derived from heavy chain antibodies (HcAb) exclusive to Camelids. Although sdAbs have been evaluated for therapeutic and imaging applications, sdAb specific to human CD20 are not believed to have been previously been described. Most current CD20 immuno-reagents are mAbs and their scFv derivatives. Due to their smaller size, sdAbs have improved tumor penetration compared to full length conventional antibodies. An additional consequence of this property is their rapid normal tissue clearance, making them compatible for use with short half-life radionuclides such as 68Ga and 18F for PET imaging and 211At for targeted radiotherapy (Vaneycken et al., 2011; Pruszynski et al., 2012). SdAbs are able to direct treatment to the tumors with minimal off target impact, which should greatly enhance the prospects for patients.

BRIEF SUMMARY

Described herein is the development of recombinant single domain antibodies, also known as nanobodies, that may provide better therapeutic results or be useful for diagnostic applications of B-cell lymphomas, or in other applications where an antibody to CD20 may be useful.

Aspects of this work are described in Jinny L. Liu, Dan Zabetakis, Ellen R. Goldman, George P. Anderson, "Selection and characterization of single domain antibodies against human CD20," *Molecular Immunology*, Volume 78, October 2016, Pages 146-154 and accompanying Supplementary Information, incorporated herein by reference for additional details on the technology described herein.

In one embodiment, and isolated anti-CD20 single domain antibody includes the amino acid sequence of SEQ ID NO: 2, SEQ ID NO: 5, or SEQ ID NO: 6.

In another embodiment, a pharmaceutical composition includes an isolated anti-CD20 single domain antibody comprising the amino acid sequence of SEQ ID NO: 2, SEQ ID NO: 5, or SEQ ID NO: 6; and a pharmaceutically acceptable carrier.

BRIEF DESCRIPTION OF THE DRAWINGS

FIG. 1 is an alignment of consensus sequences for three classes of sdAbs binding to CD20. Class A binders have longest CDR3 sequences (a.a. 96-109), Class C binders with a shorter CDR3 sequence (a.a. 96-105), and Class D have CDR 3 sequence (a.a. 96-103).

FIGS. 2A-2C show analysis of immunostaining cells by flow cytometry. SU-DHL cells immunostained with bt-sdAbs at different concentrations were measured by flow cytometer, Accuri C6. Histograms of cells stained with Neutravidin phycoerythrin (NA-PE) were used as a negative control for each bt-sdAb. A. Cells stained with bt-M24E at different concentrations show the right shift of histograms due to more cells binding to bt-M24E, while there is no change of histograms of cells stained with bt-M112D in B. C. Cells are stained with bt-M28C sharing near identical histogram pattern with A In FIG. 3A, M24E sdAb was used for binding, while in FIG. 3B, M112D was used for the blot.

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Description

The variable domain of nanobodies with only heavy chain is composed by three diverse complementarity determining regions (CDRs) and four conserved frame regions (FRs).

The epitope binding is determined mainly by CDR3. A group of anti-CD20 nanobodies sharing unique and near identical CDR3 were selected from CD20-Hoc immune phage display library using a subtractive biopanning procedure. This group of nanobodies exhibited better differential binding signals to CD20 fusion than Hoc in a monoclonal phage ELISA. Three representative sequences were selected and subcloned for protein preparation. Prepared nanobodies were then subjected to the binding assays with CD20-Hoc fusion and full length of CD20 on B lymphoma cells.

Single domain antibodies are disclosed in, for example, U.S. Pat. Nos. 9,267,930 and 7,371,849, each incorporated herein by reference for techniques relating to single-domain antibodies and the preparation of a library thereof.

The large extracellular loop of CD20 formed by residues 142-187 is a proven target for anti-CD20 antibodies, and thus was utilized for generating sdAbs. Hoc and Soc are outer capsid proteins of T4 phage and are highly antigenic. A fusion construct CD20-Hoc was prepared to act as both an immunogen for immunizing llamas, as well as a target to select phage displayed sdAbs and evaluate isolated antibodies.

Surface plasmon resonance (SPR) and a known anti-CD20 mAb, RTX, confirmed that the CD20-Hoc fusion protein was an appropriate surrogate for the full length protein for the generation of an anti-CD20 immune response. RTX bound both immobilized CD20-Hoc and NeutrAvidin bound biotin labeled CD20 peptide, but showed no binding to immobilized Hoc when evaluated by SPR.

To raise heavy chain antibodies against CD20, two llamas were immunized with recombinant CD20-Hoc fusion. Their purified polyclonal antibodies showed a substantial differential binding to CD20-Hoc versus Soc upon evaluation by a MagPlex direct binding assay.

With the presence of an immune response towards CD20-Hoc confirmed, a phage displayed sdAb library was prepared. The DNA fragments encoding heavy chain variable region (VHH) domains containing 3 unique CDRs and 4 conserved framework regions (FRs) were obtained using PCR. Amplified fragments were purified and later cloned into a plasmid DNA for displaying VHH on the M13 phage tails as fusions with minor coat protein, pIII. A library of M13 phage-displayed sdAbs derived from llamas immunized with CD20-Hoc was developed and was approximated to have $7.5 \times 10^6$ unique colony forming units (CFUs). Library complexity was estimated through the number of transformants, taking into account that partial sequencing of the library showed 75% of the representative clones had intact and unique sequences.

RO phage amplified from the immune library was subjected to two rounds of biopanning using two methods: method 1 (M1) was the standard selection protocol, method 2 (M2) consisted of subtractive panning by pre-selecting on Hoc coated wells and including soluble Hoc during panning on immobilized CD20-Hoc. M1 was expected to enrich binders to both Hoc and CD20, while M2 with Hoc subtraction was used to specifically enrich CD20 binders. The second methods was used to ensure the success of selecting CD20 specific binders. Results indicated that both methods were able to enrich potential binders against CD20-Hoc fusions by two orders of magnitude.

Selected anti-CD20 amino acid sequences are described as follows, with sequences of particular interest shown in bold text:

```
>M210H
                                              (SEQ ID NO: 1)
EVQLQASGGGLVQVGGSLRLSCTASGSTESIKHHGWYRRAPGNQ

REWVAGISSENITNVAEAVEGRFTISRDNAKNTVYLQMNSLKVE

DTAVYYCYAQDNDYRFLHRFWGQGTQVTVSIEPKTPK

>M28C
                                              (SEQ ID NO: 2)
DVQLQASGGGLVQAGGSLRLSCAASGSTESIKHHGWYRRAPGNQ

REWVAGINSENITNVAGAVKGRFTISRDNAKNITYLQMNSLKVE

DTAVYFCYAQDNDYRFLHRFWGQGTQVITSLEPKTPK

>M28D
                                              (SEQ ID NO: 3)
DVQLQASGGGLVQAGGSLRLSCAASGSTFSIKHHGWYRRAPGNQ

REWVAGINSENITNVAGAVKGRFTISRDNAKNTVYLQMNSLKVE

DTAVYFCYAQDNDYRFLHRFWGQGTQVTVSLEPKTPK

>M29C
                                              (SEQ ID NO: 4)
DVQLQASGGGLVQAGGSLRLSCAASGSTFSIKHHGWYRRAPGNQ

REWVAGINSENITNVAGAVKGRFTISRDNAKNTVYLQMNSLKVE

DTAVYFCYAQDNDYRFLHRFWGQGTQVTVSLEPKTPK

>M112D
                                              (SEQ ID NO: 5)
DVQLQASGGGLVQAEGSLRLSCAASGSTEGIKHHGWYRRAPGNQ

REWVAGISSENITNVAEAVKGRFTISRDNAKNITYLQMNSLKVE

DTAVYYCYAQDNNYRFLHRFWGQGTQVITSLEPKTPK

>M24E
                                              (SEQ ID NO: 6)
DVQLQASGGGLVQAGGSLRLSCAASGSTESIKHHGWYRRAPGNQ

REWVAGISSENITNVAEAVKGRFTISRDNAKNITYLQMNSLKVE

DTAVYYCYAQDNDYRFLHRFWGQGTQVITSLEPKTPK

>M24H
                                              (SEQ ID NO: 7)
DVQLQASGGGLVQAGGSLRLSCAASGSTFSIKHHGWYRRAPGNQ

REWVAGISSENITNVAEAVKGRFTISRDNAKNTVYLQMNSLKVE

DTAVYYCYAQDNDYRFLHRFWGQGTQVTVSLEPKTPK

>M25D
                                              (SEQ ID NO: 8)
DVQLQASGGGLVQAGGSLRLSCAASGSTFSIKHHGWYRRAPGNQ

REWVAGISSENITNVAEAVKGRFTISRDNAKNTVYLQMNSLKVE

DTAVYYCYAQDNDYRFLHRFWGQGTQVTVSLEPKTPK

>M29A
                                              (SEQ ID NO: 9)
DVQLQASGGGLVQAGGSLRLSCAASGSTFSIKHHGWYRRAPGNQ

REWVAGISSENITNVAEAVKGRFTISRDNAKNTVYLQMNSLKVE

DTAVYYCYAQDNDYRFLHRFWGQGTQVTVSLEPKTPK

>M29B
                                              (SEQ ID NO: 10)
DVQLQASGGGLVQAGGSLRLSCAASGSTFSIKHHGWYRRAPGNQ

REWVAGISSENITNVAEAVKGRFTISRDNAKNTVYLQMNSLKVE

DTAVYYCYAQDNDYRFLHRFWGQGTQVTVSLEPKTPK
```

```
>M210A
                                    (SEQ ID NO: 11)
DVQLQASGGGLVQAGGSLRLSCAASGSTFSIKHHGWYRRAPGNQ

REWVAGISSENITNVAEAVKGRFTISRDNAKNTVYLQMNSLKVE

DTAVYYCYAQDNDYRFLHRFWGQGTQVTVSLEPKTPK

>M210B
                                    (SEQ ID NO: 12)
DVQLQASGGGLVQAGGSLRLSCAASGSTFSIKHHGWYRRAPGNQ

REWVAGISSENITNVAEAVKGRFTISRDNAKNTVYLQMNSLKVE

DTAVYYCYAQDNDYRFLHRFWGQGTQVTVSLEPKTPK

>M211C
                                    (SEQ ID NO: 13)
DVQLQASGGGLVQAGGSLRLSCAASGSTFSIKHHGWYRRAPGNQ

REWVAGISSENITNVAEAVKGRFTISRDNAKNTVYLQMNSLKVE

DTAVYYCYAQDNDYRFLHRFWGQGTQVTVSLEPKTPK

>M211H
                                    (SEQ ID NO: 14)
DVQLQASGGGLVQAGGSLRLSCAASGSTFSIKHHGWYRRAPGNQ

REWVAGISSENITNVAEAVKGRFTISRDNAKNTVYLQMNSLKVE

DTAVYYCYAQDNDYRFLHRFWGQGTQVTVSLEPKTPK

>M212C
                                    (SEQ ID NO: 15)
DVQLQASGGGLVQAGGSLRLSCAASGSTFSIKHHGWYRRAPGNQ

REWVAGISSENITNVAEAVKGRFTISRDNAKNTVYLQMNSLKVE

DTAVYYCYAQDNDYRFLHRFWGQGTQVTVSLEPKTPK
```

An analysis of the above sequences was conducted through sequence alignment (FIG. 1). The CDR3 consensus sequence YAQDNDYRFLHRFW (residues 96-109) (SEQ ID NO: 16) is also shown in FIG. 1.

Figure 2A:
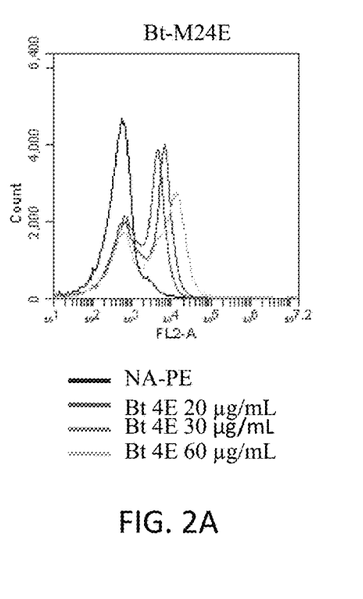
Figure 2B:
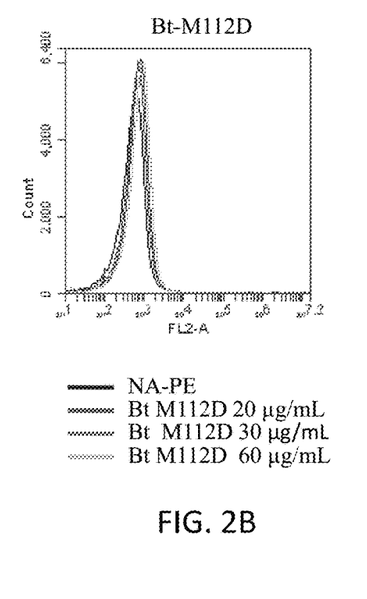
Figure 2C:
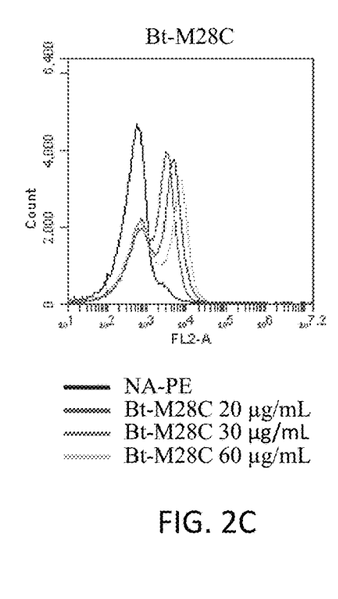
Figure 3A:
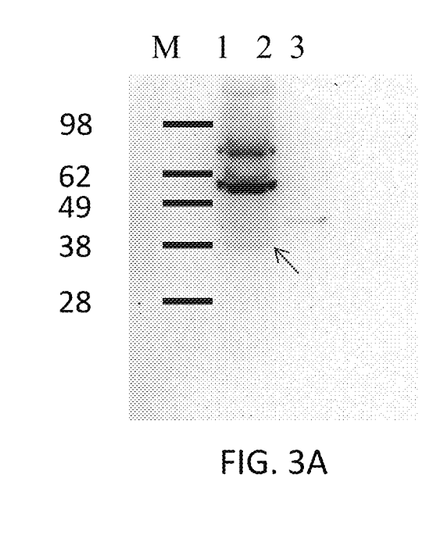
FIGS. 3A and 3B show analysis of sdAb binding to denatured CD20 in DHL-4 cells by western blotting. Su-DHL cells were harvested and lysed by the RIPA buffer supplemented with protease inhibitors. Approximately 1E+7 cells were loaded to lane 1 in each blot. Approximately 4.5 μg of purified CD20-Hoc and Hoc were loaded to lanes 2 and 3 in each blot, respectively.
Figure 3B:
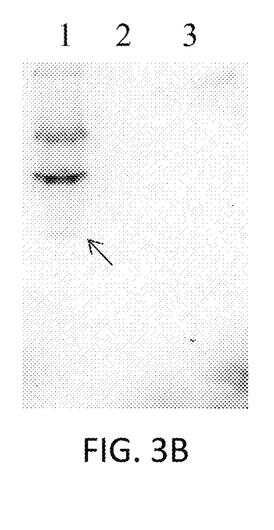

Three representative clones, M24E, M28C and M112D, were subcloned to pet22b for protein preparation. Purified proteins were able to bind to CD20-Hoc fusion better than Hoc using SPR measurements (data not shown). The purified proteins, except M112D, were able to bind to full length of native CD20 and denatured CD20 on B-lymphoma cells (FIGS. 2A-2C and 3A and 3B). These results indicate that the mutation D101 to N101 in M112D completely abolishes the binding, but does not eliminate the binding to denatured CD20.

The binding kinetics show 3 orders of magnitude higher differential binding to CD20-Hoc fusion than Hoc for M24E and M28C and approximately 100 fold for M112D. Table 1 below shows data from some of the selected clones.

TABLE 1

Affinity measurements for anti-CD20 sdAbs by SPR.

| Clone | Hoc-CD Binding Affinity | | | Hoc Binding Affinity | | | Ratio |
|---|---|---|---|---|---|---|---|
| | $k_a$ (1/Ms) | $k_d$ (1/s) | $K_D$ (M) | $k_a$ (1/Ms) | $k_d$ (1/s) | $K_D$ (M) | Hoc $K_D$/Hoc-CD20 $K_D$ |
| M28C | $3.0 \times 10^5$ | $4.5 \times 10^{-3}$ | $1.5 \times 10^{-8}$ | $6.8 \times 10^4$ | $3.6 \times 10^{-1}$ | $5.3 \times 10^{-6}$ | 353:1 |
| M24E | $7.5 \times 10^5$ | $4.3 \times 10^{-3}$ | $5.7 \times 10^{-9}$ | $2.0 \times 10^5$ | $4.6 \times 10^{-2}$ | $2.3 \times 10^{-7}$ | 40:1 |
| M112D | $2.8 \times 10^5$ | $7.0 \times 10^{-3}$ | $2.6 \times 10^{-8}$ | $1.5 \times 10^5$ | $3.2 \times 10^{-1}$ | $2.1 \times 10^{-6}$ | 81:1 |

The melting temperatures (Tms) are higher for M24E and M28C and lower in M112D (Table 2)

TABLE 2

SdAb melting point (Tm) measurement.

| Class | Name | Tm (° C.) |
|---|---|---|
| A | M24E | 56 |
| A | M28C | 52 |
| A | M112D | 49 |

Advantages

These nanobodies and their derivatives are reagents are expected to be of use in diagnostic assays and therapeutic applications. Nanobodies are small and have better penetration to tissues than conventional antibodies for diagnostic and therapeutic applications during the treatment of B-cell lymphomas. Their fusion with streptavidin or its derivatives are expected to have a higher affinity for, and allow for a more sensitive diagnostic test compared to existing antibodies.

Moreover, nanobodies are highly stable and soluble for long shelf life and can survive harsh radiolabeling conditions for imaging or radiotherapeutics.

Finally, they can be produced in bacteria or yeast, dramatically reducing costs of production as compared to production using mammalian cells.

Concluding Remarks

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

Goldman, E. R., Anderson, G. P., Liu, J. L., Delehanty, J. B., Sherwood, L. J.,
Osborn, L. E., Cummins, L. B., Hayhurst, A., 2006. Facile generation of heat-stable antiviral and antitoxin single domain antibodies from a semisynthetic llama library. Anal. Chem. 78, 8245-8255.
Liu, J. L., Zabetakis, D., Goldman, E. R., Anderson, G. P., 2013. Selection and evaluation of single domain antibodies toward MS2 phage and coat protein. Mol. Immunol. 53, 118-125.
Liu, Dan Zabetakis, Ellen R. Goldman, George P. Anderson, "Selection and characterization of single domain antibodies against human CD20," *Molecular Immunology*, Volume 78, October 2016, Pages 146-154

Pruszynski, M., Koumarianou, E., Vaidyanathan, G., Revets, H., Devoogdt, N., Lahoutte, T., Zalutsky, M. R., 2013. Targeting breast carcinoma with radio iodinated anti-HER2 nanobody. Nucl. Med. Biol. 40, 52-59.

Vaneycken, I., Devoogdt, N., Van Gassen, N., Vincke, C., Xavier, C., Wernery, U., Muyldermans, S., Lahoutte, T., Caveliers, V., 2011. Preclinical screening of anti-HER2 nanobodies for molecular imaging of breast cancer. FASEB J. 25, 2433-2446.

What is claimed is:

1. An isolated anti-CD20 single domain antibody comprising the amino acid sequence of SEQ ID NO: 2, SEQ ID NO: 5, or SEQ ID NO: 6.

2. The isolated anti-CD20 single domain antibody of claim 1, wherein the amino acid sequence is that of SEQ ID NO: 2 or SEQ ID NO: 6.

3. An isolated anti-CD20 single domain antibody comprising the amino acid sequence of SEQ ID NO: 16.

4. A pharmaceutical composition comprising:
   an isolated anti-CD20 single domain antibody comprising the amino acid sequence of SEQ ID NO: 2, SEQ ID NO: 5, or SEQ ID NO: 6;
   and a pharmaceutically acceptable carrier.

5. The pharmaceutical composition of claim 4, wherein the amino acid sequence is that of SEQ ID NO: 2 or SEQ ID NO: 6.

6. A pharmaceutical composition comprising:
an isolated anti-CD20 single domain antibody comprising the amino acid sequence of SEQ ID NO: 16;
and a pharmaceutically acceptable carrier.

* * * * *

SEQUENCE LISTING

```
<160> NUMBER OF SEQ ID NOS: 16

<210> SEQ ID NO 1
<211> LENGTH: 125
<212> TYPE: PRT
<213> ORGANISM: Artificial Sequence
<220> FEATURE:
<223> OTHER INFORMATION: synthetic construct

<400> SEQUENCE: 1

Glu Val Gln Leu Gln Ala Ser Gly Gly Gly Leu Val Gln Val Gly Gly
1               5                   10                  15

Ser Leu Arg Leu Ser Cys Thr Ala Ser Gly Ser Thr Phe Ser Ile Lys
            20                  25                  30

His His Gly Trp Tyr Arg Arg Ala Pro Gly Asn Gln Arg Glu Trp Val
        35                  40                  45

Ala Gly Ile Ser Ser Glu Asn Ile Thr Asn Val Ala Glu Ala Val Glu
    50                  55                  60

Gly Arg Phe Thr Ile Ser Arg Asp Asn Ala Lys Asn Thr Val Tyr Leu
65                  70                  75                  80

Gln Met Asn Ser Leu Lys Val Glu Asp Thr Ala Val Tyr Tyr Cys Tyr
                85                  90                  95

Ala Gln Asp Asn Asp Tyr Arg Phe Leu His Arg Phe Trp Gly Gln Gly
            100                 105                 110

Thr Gln Val Thr Val Ser Ile Glu Pro Lys Thr Pro Lys
        115                 120                 125

<210> SEQ ID NO 2
<211> LENGTH: 125
<212> TYPE: PRT
<213> ORGANISM: Artificial Sequence
<220> FEATURE:
<223> OTHER INFORMATION: synthetic construct

<400> SEQUENCE: 2

Asp Val Gln Leu Gln Ala Ser Gly Gly Gly Leu Val Gln Ala Gly Gly
1               5                   10                  15

Ser Leu Arg Leu Ser Cys Ala Ala Ser Gly Ser Thr Phe Ser Ile Lys
            20                  25                  30

His His Gly Trp Tyr Arg Arg Ala Pro Gly Asn Gln Arg Glu Trp Val
        35                  40                  45

Ala Gly Ile Asn Ser Glu Asn Ile Thr Asn Val Ala Gly Ala Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Val Glu Asp Thr Ala Val Tyr Phe Cys Tyr
                85                  90                  95

Ala Gln Asp Asn Asp Tyr Arg Phe Leu His Arg Phe Trp Gly Gln Gly
            100                 105                 110

Thr Gln Val Thr Val Ser Leu Glu Pro Lys Thr Pro Lys
        115                 120                 125
```

<210> SEQ ID NO 3
<211> LENGTH: 125
<212> TYPE: PRT
<213> ORGANISM: Artificial Sequence
<220> FEATURE:
<223> OTHER INFORMATION: synthetic construct

<400> SEQUENCE: 3

```
Asp Val Gln Leu Gln Ala Ser Gly Gly Gly Leu Val Gln Ala Gly Gly
1               5                   10                  15

Ser Leu Arg Leu Ser Cys Ala Ala Ser Gly Ser Thr Phe Ser Ile Lys
            20                  25                  30

His His Gly Trp Tyr Arg Arg Ala Pro Gly Asn Gln Arg Glu Trp Val
        35                  40                  45

Ala Gly Ile Asn Ser Glu Asn Ile Thr Asn Val Ala Gly Ala Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Val Glu Asp Thr Ala Val Tyr Phe Cys Tyr
                85                  90                  95

Ala Gln Asp Asn Asp Tyr Arg Phe Leu His Arg Phe Trp Gly Gln Gly
            100                 105                 110

Thr Gln Val Thr Val Ser Leu Glu Pro Lys Thr Pro Lys
        115                 120                 125
```

<210> SEQ ID NO 4
<211> LENGTH: 125
<212> TYPE: PRT
<213> ORGANISM: Artificial Sequence
<220> FEATURE:
<223> OTHER INFORMATION: synthetic construct

<400> SEQUENCE: 4

```
Asp Val Gln Leu Gln Ala Ser Gly Gly Gly Leu Val Gln Ala Gly Gly
1               5                   10                  15

Ser Leu Arg Leu Ser Cys Ala Ala Ser Gly Ser Thr Phe Ser Ile Lys
            20                  25                  30

His His Gly Trp Tyr Arg Arg Ala Pro Gly Asn Gln Arg Glu Trp Val
        35                  40                  45

Ala Gly Ile Asn Ser Glu Asn Ile Thr Asn Val Ala Gly Ala Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Val Glu Asp Thr Ala Val Tyr Phe Cys Tyr
                85                  90                  95

Ala Gln Asp Asn Asp Tyr Arg Phe Leu His Arg Phe Trp Gly Gln Gly
            100                 105                 110

Thr Gln Val Thr Val Ser Leu Glu Pro Lys Thr Pro Lys
        115                 120                 125
```

<210> SEQ ID NO 5
<211> LENGTH: 125
<212> TYPE: PRT
<213> ORGANISM: Artificial Sequence
<220> FEATURE:
<223> OTHER INFORMATION: artificial sequence

<400> SEQUENCE: 5

```
Asp Val Gln Leu Gln Ala Ser Gly Gly Gly Leu Val Gln Ala Glu Gly
1               5                   10                  15
```

```
Ser Leu Arg Leu Ser Cys Ala Ala Ser Gly Ser Thr Phe Gly Ile Lys
        20                  25                  30

His His Gly Trp Tyr Arg Arg Ala Pro Gly Asn Gln Arg Glu Trp Val
            35                  40                  45

Ala Gly Ile Ser Ser Glu Asn Ile Thr Asn Val Ala Glu Ala Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Val Glu Asp Thr Ala Val Tyr Tyr Cys Tyr
                 85                  90                  95

Ala Gln Asp Asn Asn Tyr Arg Phe Leu His Arg Phe Trp Gly Gln Gly
            100                 105                 110

Thr Gln Val Thr Val Ser Leu Glu Pro Lys Thr Pro Lys
        115                 120                 125
```

<210> SEQ ID NO 6
<211> LENGTH: 125
<212> TYPE: PRT
<213> ORGANISM: Artificial Sequence
<220> FEATURE:
<223> OTHER INFORMATION: artificial sequence

<400> SEQUENCE: 6

```
Asp Val Gln Leu Gln Ala Ser Gly Gly Gly Leu Val Gln Ala Gly Gly
 1               5                  10                  15

Ser Leu Arg Leu Ser Cys Ala Ala Ser Gly Ser Thr Phe Ser Ile Lys
        20                  25                  30

His His Gly Trp Tyr Arg Arg Ala Pro Gly Asn Gln Arg Glu Trp Val
            35                  40                  45

Ala Gly Ile Ser Ser Glu Asn Ile Thr Asn Val Ala Glu Ala Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Val Glu Asp Thr Ala Val Tyr Tyr Cys Tyr
                 85                  90                  95

Ala Gln Asp Asn Asp Tyr Arg Phe Leu His Arg Phe Trp Gly Gln Gly
            100                 105                 110

Thr Gln Val Thr Val Ser Leu Glu Pro Lys Thr Pro Lys
        115                 120                 125
```

<210> SEQ ID NO 7
<211> LENGTH: 125
<212> TYPE: PRT
<213> ORGANISM: Artificial Sequence
<220> FEATURE:
<223> OTHER INFORMATION: artificial sequence

<400> SEQUENCE: 7

```
Asp Val Gln Leu Gln Ala Ser Gly Gly Gly Leu Val Gln Ala Gly Gly
 1               5                  10                  15

Ser Leu Arg Leu Ser Cys Ala Ala Ser Gly Ser Thr Phe Ser Ile Lys
        20                  25                  30

His His Gly Trp Tyr Arg Arg Ala Pro Gly Asn Gln Arg Glu Trp Val
            35                  40                  45

Ala Gly Ile Ser Ser Glu Asn Ile Thr Asn Val Ala Glu Ala Val Lys
 50                  55                  60

Gly Arg Phe Thr Ile Ser Arg Asp Asn Ala Lys Asn Thr Val Tyr Leu
 65                  70                  75                  80
```

```
                65                  70                  75                  80
Gln Met Asn Ser Leu Lys Val Glu Asp Thr Ala Val Tyr Tyr Cys Tyr
                    85                  90                  95

Ala Gln Asp Asn Asp Tyr Arg Phe Leu His Arg Phe Trp Gly Gln Gly
                100                 105                 110

Thr Gln Val Thr Val Ser Leu Glu Pro Lys Thr Pro Lys
                115                 120                 125

<210> SEQ ID NO 8
<211> LENGTH: 125
<212> TYPE: PRT
<213> ORGANISM: Artificial Sequence
<220> FEATURE:
<223> OTHER INFORMATION: artificial sequence

<400> SEQUENCE: 8

Asp Val Gln Leu Gln Ala Ser Gly Gly Gly Leu Val Gln Ala Gly Gly
1               5                   10                  15

Ser Leu Arg Leu Ser Cys Ala Ala Ser Gly Ser Thr Phe Ser Ile Lys
                20                  25                  30

His His Gly Trp Tyr Arg Arg Ala Pro Gly Asn Gln Arg Glu Trp Val
                35                  40                  45

Ala Gly Ile Ser Ser Glu Asn Ile Thr Asn Val Ala Glu Ala Val Lys
                50                  55                  60

Gly Arg Phe Thr Ile Ser Arg Asp Asn Ala Lys Asn Thr Val Tyr Leu
65                  70                  75                  80

Gln Met Asn Ser Leu Lys Val Glu Asp Thr Ala Val Tyr Tyr Cys Tyr
                    85                  90                  95

Ala Gln Asp Asn Asp Tyr Arg Phe Leu His Arg Phe Trp Gly Gln Gly
                100                 105                 110

Thr Gln Val Thr Val Ser Leu Glu Pro Lys Thr Pro Lys
                115                 120                 125

<210> SEQ ID NO 9
<211> LENGTH: 125
<212> TYPE: PRT
<213> ORGANISM: Artificial Sequence
<220> FEATURE:
<223> OTHER INFORMATION: artificial sequence

<400> SEQUENCE: 9

Asp Val Gln Leu Gln Ala Ser Gly Gly Gly Leu Val Gln Ala Gly Gly
1               5                   10                  15

Ser Leu Arg Leu Ser Cys Ala Ala Ser Gly Ser Thr Phe Ser Ile Lys
                20                  25                  30

His His Gly Trp Tyr Arg Arg Ala Pro Gly Asn Gln Arg Glu Trp Val
                35                  40                  45

Ala Gly Ile Ser Ser Glu Asn Ile Thr Asn Val Ala Glu Ala Val Lys
                50                  55                  60

Gly Arg Phe Thr Ile Ser Arg Asp Asn Ala Lys Asn Thr Val Tyr Leu
65                  70                  75                  80

Gln Met Asn Ser Leu Lys Val Glu Asp Thr Ala Val Tyr Tyr Cys Tyr
                    85                  90                  95

Ala Gln Asp Asn Asp Tyr Arg Phe Leu His Arg Phe Trp Gly Gln Gly
                100                 105                 110

Thr Gln Val Thr Val Ser Leu Glu Pro Lys Thr Pro Lys
                115                 120                 125
```

<210> SEQ ID NO 10
<211> LENGTH: 125
<212> TYPE: PRT
<213> ORGANISM: Artificial Sequence
<220> FEATURE:
<223> OTHER INFORMATION: artificial sequence

<400> SEQUENCE: 10

```
Asp Val Gln Leu Gln Ala Ser Gly Gly Gly Leu Val Gln Ala Gly Gly
1               5                   10                  15

Ser Leu Arg Leu Ser Cys Ala Ala Ser Gly Ser Thr Phe Ser Ile Lys
            20                  25                  30

His His Gly Trp Tyr Arg Arg Ala Pro Gly Asn Gln Arg Glu Trp Val
        35                  40                  45

Ala Gly Ile Ser Ser Glu Asn Ile Thr Asn Val Ala Glu Ala Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Val Glu Asp Thr Ala Val Tyr Tyr Cys Tyr
                85                  90                  95

Ala Gln Asp Asn Asp Tyr Arg Phe Leu His Arg Phe Trp Gly Gln Gly
            100                 105                 110

Thr Gln Val Thr Val Ser Leu Glu Pro Lys Thr Pro Lys
        115                 120                 125
```

<210> SEQ ID NO 11
<211> LENGTH: 125
<212> TYPE: PRT
<213> ORGANISM: Artificial Sequence
<220> FEATURE:
<223> OTHER INFORMATION: artificial sequence

<400> SEQUENCE: 11

```
Asp Val Gln Leu Gln Ala Ser Gly Gly Gly Leu Val Gln Ala Gly Gly
1               5                   10                  15

Ser Leu Arg Leu Ser Cys Ala Ala Ser Gly Ser Thr Phe Ser Ile Lys
            20                  25                  30

His His Gly Trp Tyr Arg Arg Ala Pro Gly Asn Gln Arg Glu Trp Val
        35                  40                  45

Ala Gly Ile Ser Ser Glu Asn Ile Thr Asn Val Ala Glu Ala Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Val Glu Asp Thr Ala Val Tyr Tyr Cys Tyr
                85                  90                  95

Ala Gln Asp Asn Asp Tyr Arg Phe Leu His Arg Phe Trp Gly Gln Gly
            100                 105                 110

Thr Gln Val Thr Val Ser Leu Glu Pro Lys Thr Pro Lys
        115                 120                 125
```

<210> SEQ ID NO 12
<211> LENGTH: 125
<212> TYPE: PRT
<213> ORGANISM: Artificial Sequence
<220> FEATURE:
<223> OTHER INFORMATION: artificial sequence

<400> SEQUENCE: 12

```
Asp Val Gln Leu Gln Ala Ser Gly Gly Gly Leu Val Gln Ala Gly Gly
```

```
                1               5                   10                  15
            Ser Leu Arg Leu Ser Cys Ala Ala Ser Gly Ser Thr Phe Ser Ile Lys
                        20                  25                  30

His His Gly Trp Tyr Arg Arg Ala Pro Gly Asn Gln Arg Glu Trp Val
                        35                  40                  45

Ala Gly Ile Ser Ser Glu Asn Ile Thr Asn Val Ala Glu Ala Val Lys
                        50                  55                  60

Gly Arg Phe Thr Ile Ser Arg Asp Asn Ala Lys Asn Thr Val Tyr Leu
            65                  70                  75                  80

Gln Met Asn Ser Leu Lys Val Glu Asp Thr Ala Val Tyr Tyr Cys Tyr
                        85                  90                  95

Ala Gln Asp Asn Asp Tyr Arg Phe Leu His Arg Phe Trp Gly Gln Gly
                        100                 105                 110

Thr Gln Val Thr Val Ser Leu Glu Pro Lys Thr Pro Lys
                        115                 120                 125

<210> SEQ ID NO 13
<211> LENGTH: 125
<212> TYPE: PRT
<213> ORGANISM: Artificial Sequence
<220> FEATURE:
<223> OTHER INFORMATION: artificial sequence

<400> SEQUENCE: 13

Asp Val Gln Leu Gln Ala Ser Gly Gly Gly Leu Val Gln Ala Gly Gly
            1               5                   10                  15

Ser Leu Arg Leu Ser Cys Ala Ala Ser Gly Ser Thr Phe Ser Ile Lys
                        20                  25                  30

His His Gly Trp Tyr Arg Arg Ala Pro Gly Asn Gln Arg Glu Trp Val
                        35                  40                  45

Ala Gly Ile Ser Ser Glu Asn Ile Thr Asn Val Ala Glu Ala Val Lys
                        50                  55                  60

Gly Arg Phe Thr Ile Ser Arg Asp Asn Ala Lys Asn Thr Val Tyr Leu
            65                  70                  75                  80

Gln Met Asn Ser Leu Lys Val Glu Asp Thr Ala Val Tyr Tyr Cys Tyr
                        85                  90                  95

Ala Gln Asp Asn Asp Tyr Arg Phe Leu His Arg Phe Trp Gly Gln Gly
                        100                 105                 110

Thr Gln Val Thr Val Ser Leu Glu Pro Lys Thr Pro Lys
                        115                 120                 125

<210> SEQ ID NO 14
<211> LENGTH: 125
<212> TYPE: PRT
<213> ORGANISM: Artificial Sequence
<220> FEATURE:
<223> OTHER INFORMATION: artificial sequence

<400> SEQUENCE: 14

Asp Val Gln Leu Gln Ala Ser Gly Gly Gly Leu Val Gln Ala Gly Gly
            1               5                   10                  15
```

```
Ser Leu Arg Leu Ser Cys Ala Ala Ser Gly Ser Thr Phe Ser Ile Lys
            20                  25                  30

His His Gly Trp Tyr Arg Arg Ala Pro Gly Asn Gln Arg Glu Trp Val
            35                  40                  45

Ala Gly Ile Ser Ser Glu Asn Ile Thr Asn Val Ala Glu Ala Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Val Glu Asp Thr Ala Val Tyr Tyr Cys Tyr
                 85                  90                  95

Ala Gln Asp Asn Asp Tyr Arg Phe Leu His Arg Phe Trp Gly Gln Gly
                100                 105                 110

Thr Gln Val Thr Val Ser Leu Glu Pro Lys Thr Pro Lys
            115                 120                 125

<210> SEQ ID NO 15
<211> LENGTH: 125
<212> TYPE: PRT
<213> ORGANISM: Artificial Sequence
<220> FEATURE:
<223> OTHER INFORMATION: artificial sequence

<400> SEQUENCE: 15

Asp Val Gln Leu Gln Ala Ser Gly Gly Gly Leu Val Gln Ala Gly Gly
 1               5                  10                  15

Ser Leu Arg Leu Ser Cys Ala Ala Ser Gly Ser Thr Phe Ser Ile Lys
            20                  25                  30

His His Gly Trp Tyr Arg Arg Ala Pro Gly Asn Gln Arg Glu Trp Val
            35                  40                  45

Ala Gly Ile Ser Ser Glu Asn Ile Thr Asn Val Ala Glu Ala Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Val Glu Asp Thr Ala Val Tyr Tyr Cys Tyr
                 85                  90                  95

Ala Gln Asp Asn Asp Tyr Arg Phe Leu His Arg Phe Trp Gly Gln Gly
                100                 105                 110

Thr Gln Val Thr Val Ser Leu Glu Pro Lys Thr Pro Lys
            115                 120                 125

<210> SEQ ID NO 16
<211> LENGTH: 14
<212> TYPE: PRT
<213> ORGANISM: Artificial Sequence
<220> FEATURE:
<223> OTHER INFORMATION: artificial sequence

<400> SEQUENCE: 16

Tyr Ala Gln Asp Asn Asp Tyr Arg Phe Leu His Arg Phe Trp
 1               5                  10
```